(12) United States Patent
Freidberg et al.

(10) Patent No.: US 6,699,277 B1
(45) Date of Patent: Mar. 2, 2004

(54) STENT WITH COVER CONNECTORS

(75) Inventors: Carlos Vonderwalde Freidberg, Richmond (CA); Daniel Capuano, Hulxquilucan (MX)

(73) Assignee: Diseno y Desarrollo Medica, S.A. de C.V., San Luis Potosi (MX)

( * ) Notice: Subject to any disclaimer, the term of this patent is extended or adjusted under 35 U.S.C. 154(b) by 382 days.

(21) Appl. No.: 09/664,999

(22) Filed: Sep. 18, 2000

Related U.S. Application Data

(63) Continuation-in-part of application No. 09/522,336, filed on Mar. 9, 2000.

(51) Int. Cl.$^7$ ................................................ A61F 2/06
(52) U.S. Cl. ................................................... 623/1.13
(58) Field of Search .......................... 623/1.12–1.14, 623/1.15, 1.25, 1.23, 1.1, 1.35, 1.36

(56) References Cited

U.S. PATENT DOCUMENTS

| | | | |
|---|---|---|---|
| 5,607,444 A | 3/1997 | Lam | 606/194 |
| 5,667,523 A | 9/1997 | Bynon et al. | 606/198 |
| 5,709,713 A | 1/1998 | Evans et al. | 623/1 |
| 5,769,882 A | 6/1998 | Fogarty et al. | 623/1 |
| 5,769,887 A | 6/1998 | Brown et al. | 623/1 |
| 5,782,904 A | 7/1998 | White et al. | 623/1 |
| 5,865,723 A | 2/1999 | Love | 600/36 |
| 5,897,589 A | 4/1999 | Cottenceau et al. | 623/1 |
| 5,935,161 A | 8/1999 | Robinson et al. | 623/1 |
| 6,042,605 A | 3/2000 | Martin et al. | 623/1 |
| 6,099,559 A | 8/2000 | Nolting | 623/1.16 |
| 6,168,619 B1 | 1/2001 | Dinh et al. | 623/1.13 |
| 6,235,054 B1 | 5/2001 | Berg et al. | 623/1.36 |

FOREIGN PATENT DOCUMENTS

| | | |
|---|---|---|
| EP | 0732089 | 9/1996 |
| EP | 0960607 | 12/1999 |
| WO | WO9944536 | 9/1999 |

*Primary Examiner*—Michael J. Milano
*Assistant Examiner*—(Jackie) Tan-Uyen T. Ho
(74) *Attorney, Agent, or Firm*—Edward J. Lynch; Duane Morris LLP

(57) ABSTRACT

A stent suitable for maintaining the patency of a bodily lumen, generally comprising a tubular body configured to facilitate connection of a cover thereto. A stent assembly of the invention generally comprises a stent having cover connectors in contact with a cover to secure the cover to a surface of the stent. The invention also comprises methods of securing a cover to a stent. In a first embodiment, the cover connector on an expandable tubular body has a first section, a second section, and a third section between the first and second sections. The connector has an open configuration, and a closed configuration in which the first section has at least one bend and the second section has at least one bend, so that the first and second sections are bent together and are directed towards the third section therebetween. In a second embodiment, a cover connector is secured to an end of the expandable tubular body, and is configured to fold from an open configuration to a closed configuration in which the connector extends toward a midpoint of the tubular body between the first and second ends of the tubular body and contacts a cover located between the cover connector and a surface of the stent, to secure the cover thereto.

10 Claims, 10 Drawing Sheets

STENT WITH COVER CONNECTORS

This application is a continuation-in-part application of U.S. patent application Ser. No. 09/522,336, entitled STENT WITH COVER CONNECTORS, filed Mar. 9, 2000, incorporated herein in its entirety by reference.

BACKGROUND OF THE INVENTION

This invention relates to the field of intraluminal support devices such as stents and the like. Typically, stents are expandable, tubular metallic devices that are positioned within a patient's vasculature or other body lumen and expanded in order to support a vessel or body lumen at a desired intraluminal location to allow the flow of blood or other body fluids therethrough. Often, the stents are formed from a deformable metal and delivered to the desired intraluminal location by mounting the stent onto an expandable portion, e.g. a balloon, on the distal extremity of a delivery catheter. By advancing the catheter through the body lumen, the stent may be delivered to a desired position and expanded therein by expanding the balloon to an expanded configuration, seating it within the artery or other body lumen. Other implementations make use of a self-expanding stent formed from a suitable material such as pseudoelastic material that is delivered in a constricted condition and when released spontaneously expands to an enlarged configuration. A stent made of superelastic alloy (e.g. NiTi alloy) may be inserted into the body lumen with a stress induced martensitic phase and expanded within the body lumen. Further details of stents and stent delivery systems may be found in U.S. Pat. No. 5,507,768 (Lau et al.), U.S. Pat. No. 5,458,615 (Klemm et al.), and U.S. Pat. No. 5,514,154 (Lau et al.), incorporated herein by reference in their entireties.

Stents are often used in conjunction with an intravascular treatment for conditions such as obstructive coronary artery disease and peripheral artery disease. For example, ablation, atherectomy, balloon dilation, laser treatment or other procedures are among the methods used to widen a stenotic region of a patient's vasculature. However, restenosis occurs in large percentage of percutaneous transluminal coronary angioplasty (PTCA) patients and rates can be even higher with other procedures. Restenosis is thought to be a natural healing reaction provoked by injury from the intravascular procedure. The healing process frequently causes thrombosis and may lead to intimal hyperplasia that occludes the vessel. The prior art has employed a number of mechanical and pharmacological strategies to reduce the restenosis rate, but none have been particularly effective. Accordingly, stents have been proposed to maintain the patency of a treated vessel and reduce restenosis. Using stents, restenosis rates have fallen to less than 20%. Although helpful in reducing restenosis, stents do not represent a complete solution. The framework of the stent may still allow migration and proliferation of the smooth muscle cells, while the stent itself can be thrombogenic. To address these problems, stents have been provided with covers made from various materials such as DACRON, polytetrafluoroethylene (PTFE), heterologous tissue and autologous veins, arteries and tissue.

It would be a significant advance to provide a stent with an improved connector for securing a cover to the stent. This invention satisfies these and other needs.

SUMMARY OF THE INVENTION

The invention is directed to a stent suitable for maintaining the patency of a bodily lumen, generally comprising a tubular body configured to facilitate connection of a cover thereto. A stent assembly of the invention generally comprises a stent having at least one cover connector on the tubular body in contact with a cover to secure the cover to a surface of the stent. The invention also comprises methods of securing a cover to a stent.

In a first embodiment, the cover connector on an expandable tubular body has a first section, a second section, and a third section between the first and second sections. The connector has an open configuration, and a closed configuration in which the first section has at least one bend and the second section has at least one bend, so that the first and second sections are bent together and are directed towards the third section therebetween. The ends of the connector are configured to pierce the cover so that at least a portion of the first and second sections extend through the cover. With the cover pierced by the first and second ends of the connector, the ends of the connector are bent together towards the third section, so that the first and second sections of the connector are adjacent an outer surface of the cover and the third section of the connector is adjacent an inner surface of the cover, to form the closed configuration. A stent assembly of the invention generally comprises a covered stent having at least a portion of the first and second sections of the cover connector extending through a cover, to secure the cover to the stent. In one embodiment the cover connector is configured to draw the lengthwise edges of a stent cover together as the connector is bent from the first to the second configuration to close the cover about the stent surface.

A method of securing a cover to a stent generally comprises piercing the first end of the cover connector at a first location on the cover and piercing the second end of the cover connector through the cover at a second location from an inner surface to an outer surface of the cover. The first and second sections of the cover connector are bent towards the third section to form the closed configuration and secure the cover to the stent.

In a second embodiment, the cover connector presses the cover against a surface of the stent to secure the cover thereto without piercing the cover. The cover connector is secured to an end of the expandable tubular body of the stent, and is configured to fold from an open configuration to a closed configuration in which the connector extends toward a midpoint of the tubular body between the first and second ends of the tubular body and contacts a cover located between the cover connector and a surface of the tubular body of the stent, to secure the cover thereto. The cover connector presses the cover against a surface of the stent to secure the cover thereto without piercing the cover. A method of securing a cover to a stent generally comprises placing a cover on the stent and folding the cover connector from the open configuration to the closed configuration so that at least a section of the cover is in contact with the cover connector and between the cover connector and a surface of the stent.

The cover connectors may be configured to secure a cover to either an inner surface or an outer surface of the tubular body of the stent. In a presently preferred embodiment, a plurality of cover connectors are provided on the stent to connect a cover which extends over a substantial portion, and preferably all of the length of the stent, in order to minimize restenosis in the body lumen.

In one embodiment, a stent is provided with eyelet members having an opening therein configured to receive a securing member such as a suture to thereby secure a cover to the stent.

The cover may be a variety of suitable materials which are preferably expandable, biocompatible, and non-thrombogenic, including autologous tissue, heterologous tissue such as bovine pericardium, porcine pericardium, aortic leaflet, and polymeric materials such as PTFE and polyesters such as DACRON. In a preferred embodiment, the cover is generally cylindrical for corresponding to the tubular framework or the stent.

The stent may be an expandable, tubular framework and may be a conventional self expanding or balloon expandable stent. A variety of stent designs may be used, including stents formed from braided tube, slotted tubes, and coils or closed sinusoidal rings of wire or ribbon, and the like.

Another embodiment of the invention comprises a stent having an expandable tubular body having a first end, a second end, a plurality of cylindrical wall sections defining an open-walled structure, and having a plurality of bar members connected to the tubular body. Each bar member is connected to and extends between longitudinally adjacent cylindrical wall sections. In one embodiment, at least one bar member is between longitudinally adjacent cylindrical wall sections. In one embodiment, the stent is part of a stent assembly including a cover having a first end, a second end, and an intermediate section between the first and second ends. The cover is disposed over at least one section of the stent and under at least a second section of the stent. For example, in one embodiment, an intermediate section of the cover is adjacent to an outer surface of the intermediate wall section of the stent, and the first end and the second end of the cover are adjacent to an inner surface of the cylindrical wall sections at the first and second ends, respectively, of the stent. In an alternative embodiment, the intermediate section of the cover is adjacent to an inner surface of the intermediate cylindrical wall section of the stent, and the first end and the second end of the cover are adjacent to an outer surface of the cylindrical wall sections at the ends of the stent. The cover is disposed between a portion of a cylindrical wall section and a bar member connecting the cylindrical wall section to a longitudinally adjacent cylindrical wall section of the tubular body. Consequently, the stent facilitates attaching the cover to the stent, and the stent assembly having a cover on the stent provides a securely attached cover, and avoids or reduces disadvantageous damage to the cover during attachment. Disposing a section of the ends of the cover between a portion of the stent tubular body and the bar member attached to that portion in accordance with the invention prevents or inhibits displacement of the cover relative to the stent during advancement or deployment of the stent assembly within a patient's body lumen. The cylindrical wall sections of the stent are thus configured as cover connectors in that the ends of the cover can be disposed between the wall section and the bar members attached thereto, and can be disposed under some wall sections while being disposed over other wall sections, to secure the cover to the stent. In a presently preferred embodiment, the cover is further secured to the stent with securing members such as suture, clips, wires, and the like. In one embodiment the stent has at least one eyelet member with an opening configured to receive a securing member therein to secure a cover to the tubular body.

The stent assembly is implanted in the patient's body lumen, typically by mounting the stent assembly on the distal extremity of a delivery catheter. Specifically, a tubular stent with a cover disposed about at least part of the stent, and secured thereto by the cover connectors, is mounted on a balloon, for a balloon expandable stent, or on a containing mechanism for a self expandable stent. The catheter is advanced through the body lumen within the patient until the distal extremity of the catheter having the stent assembly is positioned at a desired location therein. The stent assembly is expanded by expanding the balloon or releasing the containing mechanism on which the stent assembly is mounted to anchor the stent assembly within the body lumen. Once the stent assembly is effectively positioned within the body lumen, the expanded balloon may be contracted, e.g. by deflation, and then the delivery catheter may be withdrawn.

The stent having cover connectors of the invention provides for easy attachment of a stent cover onto the stent. This is particularly advantageous in the case of a cover which is impregnated with a therapeutic or diagnostic agent, such as an angiogenesis or antithrombotic agent, just before use or stored in the agent to preimpregnate the cover. The cover connectors allow the impregnated cover to be quickly and easily attached to the stent just before implantation of the stent assembly in the patient's body lumen. Thereafter, the stent assembly can be positioned at a desired site within the patient's body lumen, where the cover will release the therapeutic agent.

The cover connectors of the invention provide for improved connection of a cover to a stent surface, by providing an easily formed connection between the cover and the stent. The cover connectors of the invention avoid the use of sutures or adhesive to secure the cover to the stent, yet provide a durable, rugged, low profile connection. These and other advantages of the invention will become more apparent from the following detailed description and exemplary figures.

DETAILED DESCRIPTION OF THE INVENTION

Figure 1:
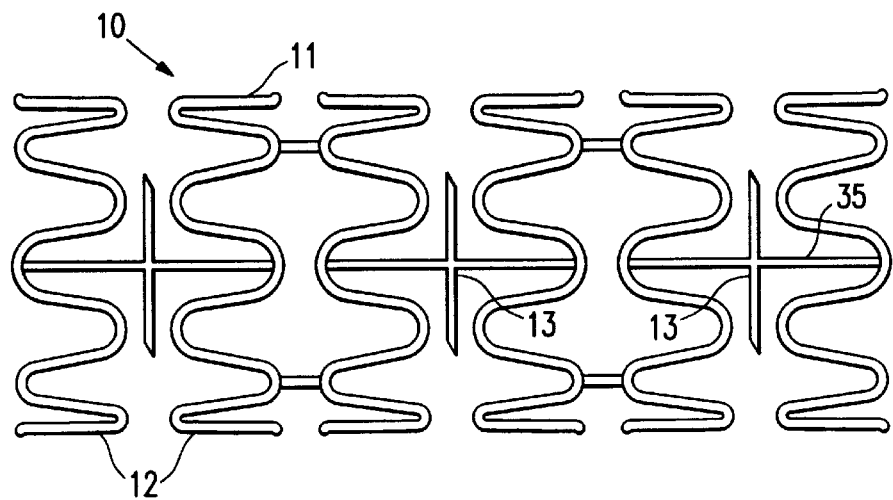
FIG. 1 is an elevational view of a stent having cover connectors which embodies features of the invention.
Figure 2:
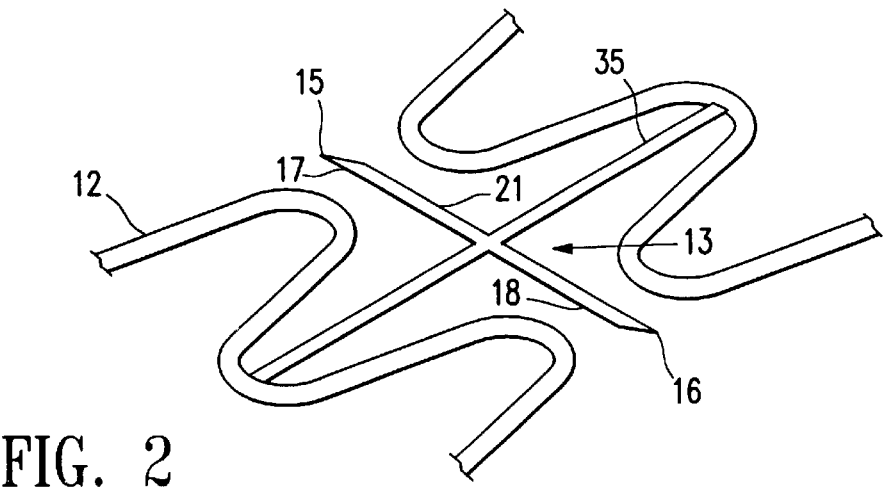
FIG. 2 is an enlarged view of the stent shown in FIG. 1, illustrating the cover connector in an open configuration.
Figure 3:
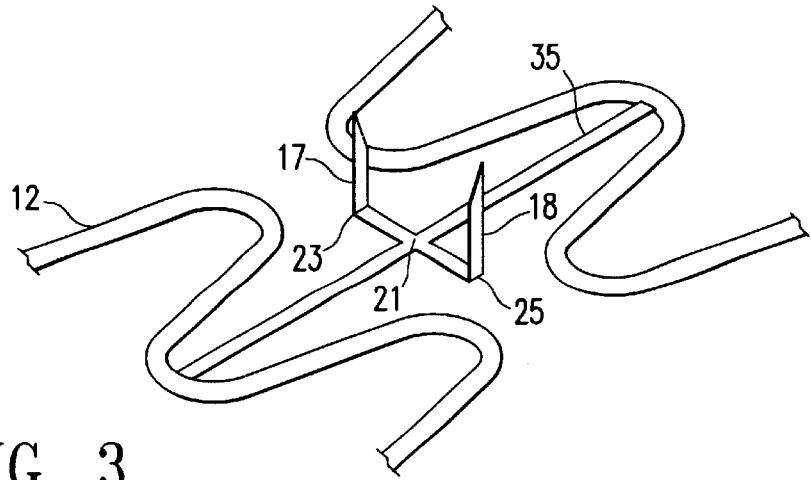
FIG. 3 illustrates the cover connector shown in FIG. 2, in a bent U-shaped configuration.
Figure 4:
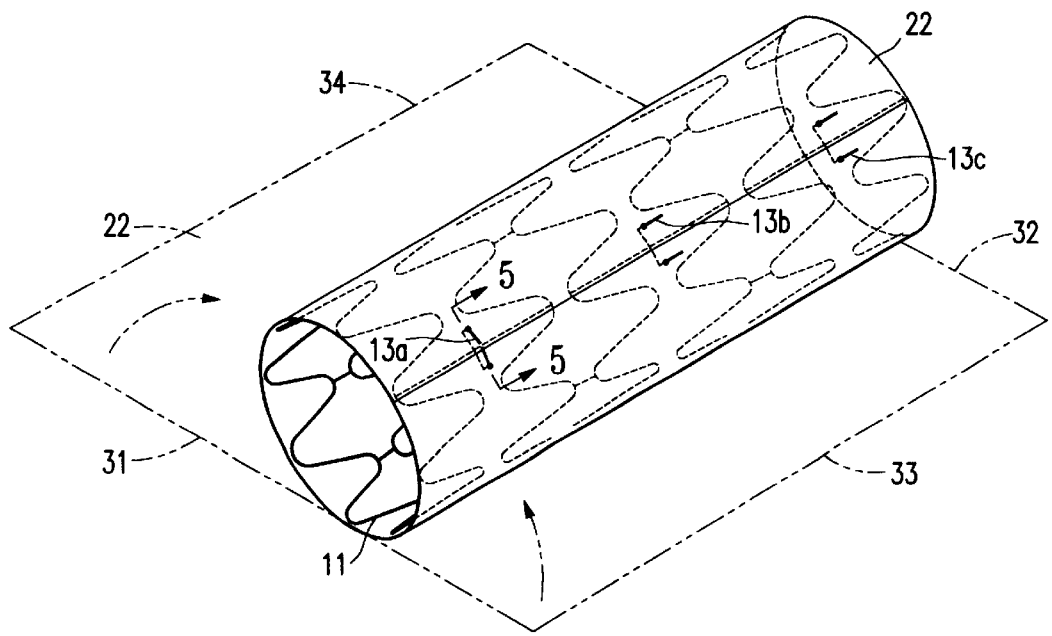
FIG. 4 is a perspective view, partially in phantom, of a stent assembly which embodies features of the invention illustrating a cover secured to the stent.
Figure 5:
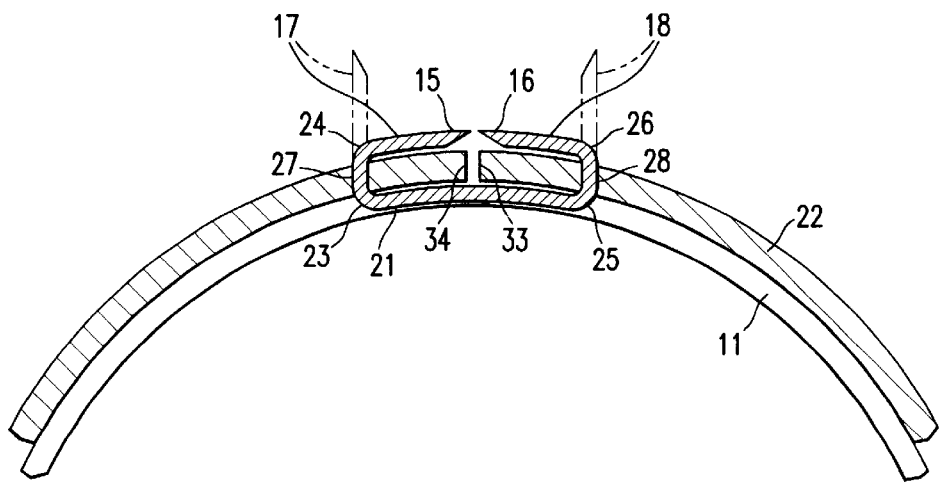
FIG. 5 is a transverse cross sectional view of the stent assembly shown in FIG. 4, taken along lines 5—5.

FIG. 1 is an elevational view of a first embodiment of a stent 10 which embodies features of the invention, comprising an expandable tubular body 11 having first and second ends, a lumen therein, and a framework of spaced apart wall sections 12 defining an open-walled structure, and cover connectors 13 on the tubular body. The cover connectors 13, which are illustrated in more detail in FIG. 2, showing an enlarged view of the connectors shown in FIG. 1, have a first end 15, a second end 16, a first section 17 adjacent to the first end 15, a second section 18 adjacent to the second end 16, and a third section 21 between the first and second sections. The connector 13 is illustrated in FIG. 2 in an open configuration in which the connector is a generally straight, pointed projection attached to the tubular body. FIG. 3 illustrates the connector shown in FIG. 2 bent into a generally U-shaped configuration which facilitates piercing the ends of the connector through a cover to be secured to the stent. The connector is bent at a first location (forming bend 23) on the first section so that at least a section of the first section is above the tubular body, and at a first location (forming bend 25) on the second section so that at least a section of the second section is above the tubular body. FIG. 4 illustrates a cover 22 pierced by the ends of the cover connector. As best illustrated in FIG. 5, showing a transverse cross section of the stent assembly shown in FIG. 4, taken along lines 5—5, the cover connector assumes the closed configuration as the first section 17 and the second section 18 are bent so that at least a portion of the first and second sections are in contact with the outer surface of the cover and the third section 21 is adjacent the inner surface of the cover. In the presently preferred embodiment illustrated in FIG. 5, the cover connector assumes the closed configuration when the first section has a first bend 23 and a second bend 24 in the same direction as the first bend in the first section, and the second section has a first bend 25 and a second bend 26 in the same direction as the first bend in the second section. However, the closed configuration can be formed by a single bend in the first section and a single bend in the second section when the angle of the bend is large enough that the first and second sections contact the outer surface of the cover (not shown).

In the embodiment illustrated in FIG. 5, the second bend 24 on the first section is between the first end 15 of the connector and the first bend 23 on the first section, and the second bend 26 on the second section is between the second end 16 of the connector and the first bend 25 on the second section. In an alternative embodiment in which the connector is configured to draw the edges of the cover together as the connector is bent into the closed configuration, the second bend 24 on the first section is between the third section 21 of the connector and the first bend 23 on the first section, and the second bend 26 on the second section is between the third section 21 of the connector and the first bend 25 on the second section. Thus, with the connector in the U-shaped configuration illustrated in phantom in FIG. 5 and the cover pierced by the first and second ends of the connector, as the connector is bent at the second location on the first and second sections to form the second bend 24, the cover will be stretched about the stent and the edges of the cover pushed together or further around the stent. Similarly, in the embodiment illustrated in FIG. 5, a portion 27 of the first section between the first and second bends thereon is directed perpendicular to the third section, and a portion 28 of the second section between the first and second bends thereon is directed perpendicular to the third section. In an alternative embodiment (not shown), after the cover 22 is placed on the connector, the portion 27 between the first and second bends on the first section and the portion 28 between the first and second bends on the second section are disposed at an angle toward the third section 21 by further bending the first bends 23 and 25 from a perpendicular angle to an acute angle, so that the edges of the cover are pushed or drawn together.

Figure 6:
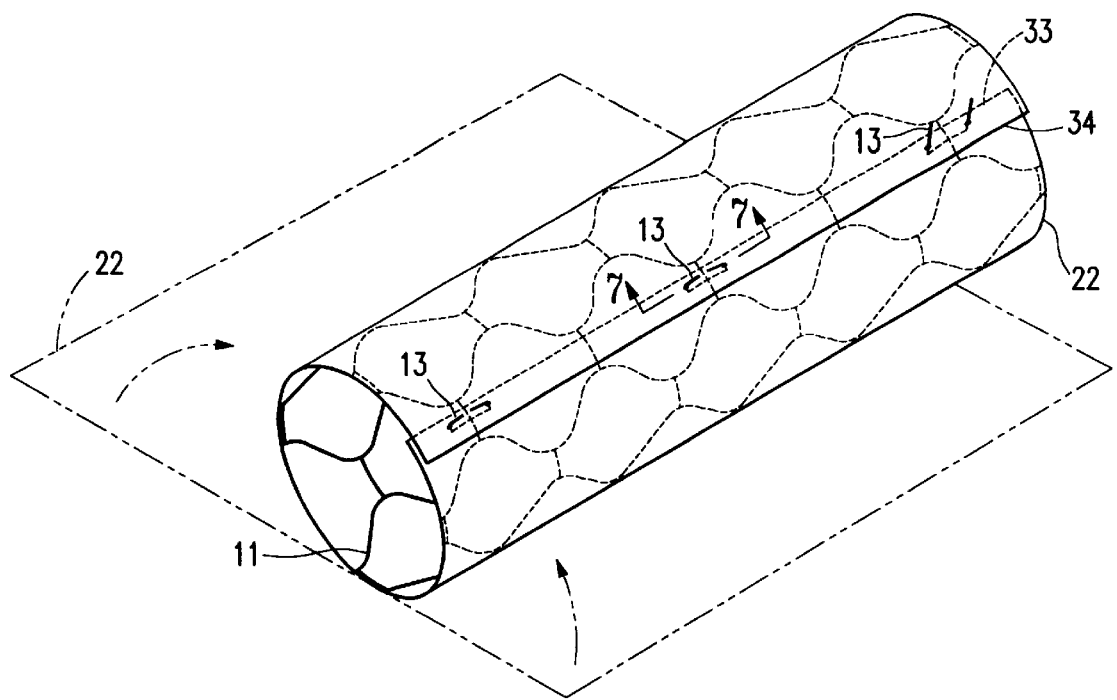
FIG. 6 is a perspective view, of an alternative embodiment of a stent assembly which embodies features of the invention, in which the cover connector is axially aligned in the open configuration with the longitudinal axis of the stent
Figure 7:
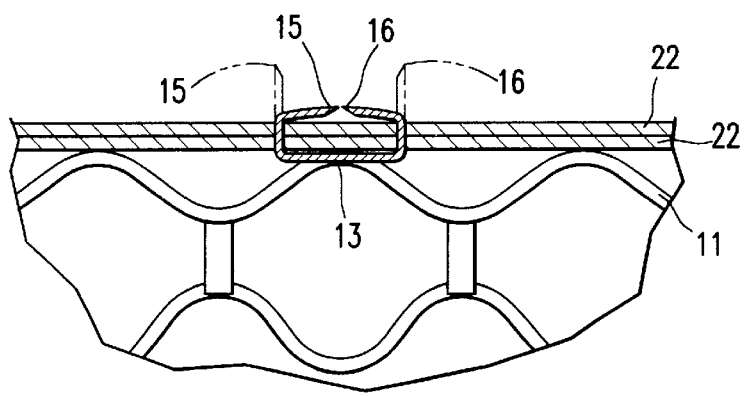
FIG. 7 is longitudinal cross sectional view of a section of the stent assembly shown in FIG. 6, taken along lines 7—7.

In FIG. 4, a first cover connector 13a is in the closed configuration, and cover connectors 13b and 13c are in the U-shaped configuration. FIG. 4 illustrates the cover 22 in phantom before being wrapped around the stent and connected thereto by the cover connectors 13. The cover 22 is in the form of a sheet of material wrapped around the stent, with a first end 31 and a second end 32, and first 33 and second 34 edges extending the length of the cover from the first to the second end thereof. In the presently preferred embodiment illustrated in FIG. 5, the two edges 33/34 of the cover corresponding to the length of the cover are abutting. However, in an alternative embodiment the edges may overlap one another as illustrated in FIGS. 6 and 7. Additionally, although the cover is illustrated as a sheet of material wrapped around the stent, the cover could be preformed into a tubular cylinder before being placed on the stent and connected thereto.

In one embodiment, the connector is optionally provided with weakened sections configured to bend, as for example by thinning or narrowing the connector at the locations configured to bend. The connector 13 has a length that is typically about 0.15 mm to about 10 mm, preferably about 0.5 mm to about 4 mm, and a width that is about 0.07 mm to about 2 mm, preferably about 0.1 mm to about 1 mm. The first and second sections have a length of about 0.1 to about 6 mm, preferably about 0.33 to about 2.6 mm. The third section has a length of about 0.05 to about 4 mm, preferably about 0.17 to about 1.4 mm.

The cover connectors may be secured to the tubular body in a variety of configurations. In the presently preferred embodiment of the invention shown in FIG. 1, the cover connector 13 is attached to a support member 35 extending between the spaced apart wall sections of the tubular body of the stent. The support member has a first end secured to the tubular body and a second end secured to the tubular body, and the third section of the connector is secured to the support member between the first and second ends of the support member. The cover connectors may be manufactured as a separate part and later joined to the tubular body, or manufactured with the tubular body as a one piece unit. The terms "secured" and "attached" as used herein to discuss the connection between the cover connectors and the tubular body should be understood to include cover connectors separately joined to the tubular body and cover connectors made as a section of the tubular body.

In a presently preferred embodiment, the connector has a longitudinal axis which is not axially aligned with the tubular body longitudinal axis. As a result, the connector can be used to secure the two edges 33/34 of the cover without the need for preattaching the edges 33/34 of the cover together to form a cylinder, or without overlapping the edges of the cover. In the presently preferred embodiment illustrated in FIG. 1, the cover connector is substantially perpendicular to the longitudinal axis of the tubular body of the stent in the open configuration. By substantially perpendicular, it should be understood that the angle the cover connector makes relative to the longitudinal axis may be 90° or somewhat different from a 90° angle, as for example by about 65° to about 115°. However, in an alternative embodiment, the cover connector may have a longitudinal axis axially aligned with the tubular body longitudinal axis. FIG. 6 and illustrate a cover connector which is directed substantially parallel to the longitudinal axis of the tubular body in the open configuration. As illustrated in FIG. 6 showing the stent with a cover being secured thereto, and FIG. 7 showing a cross section of the assembly shown in FIG. 6 taken along lines 7—7, the edges of the cover 22 are overlapping so that sections of cover adjacent to the opposite edges of the stent can be pierced by the first and second ends of the connector to secure the cover to the stent.

Figure 8:
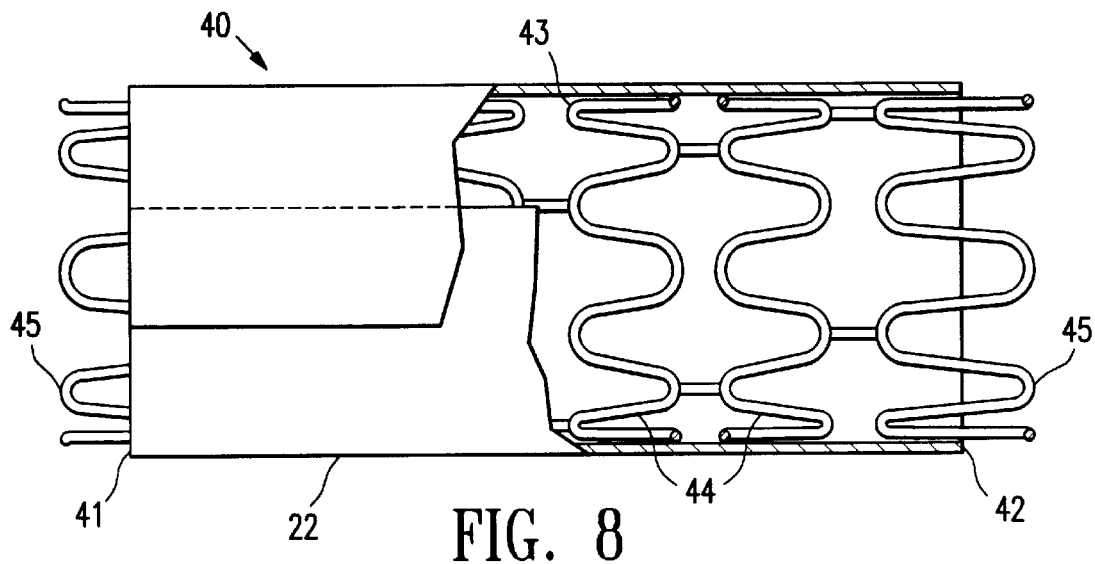
FIG. 8 is an elevational view, partially broken away and partially in section, of an alternative embodiment of a stent assembly which embodies features of the invention, having cover connectors in an open configuration on the ends of the stent.
Figure 9:
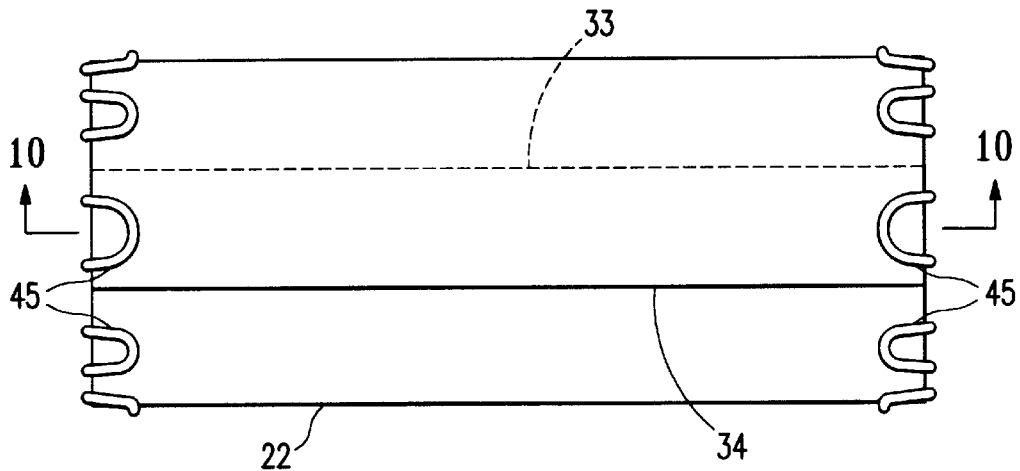
FIG. 9 is an elevational view of the stent assembly shown in FIG. 8, illustrating the cover connectors in a closed configuration.
Figure 10:
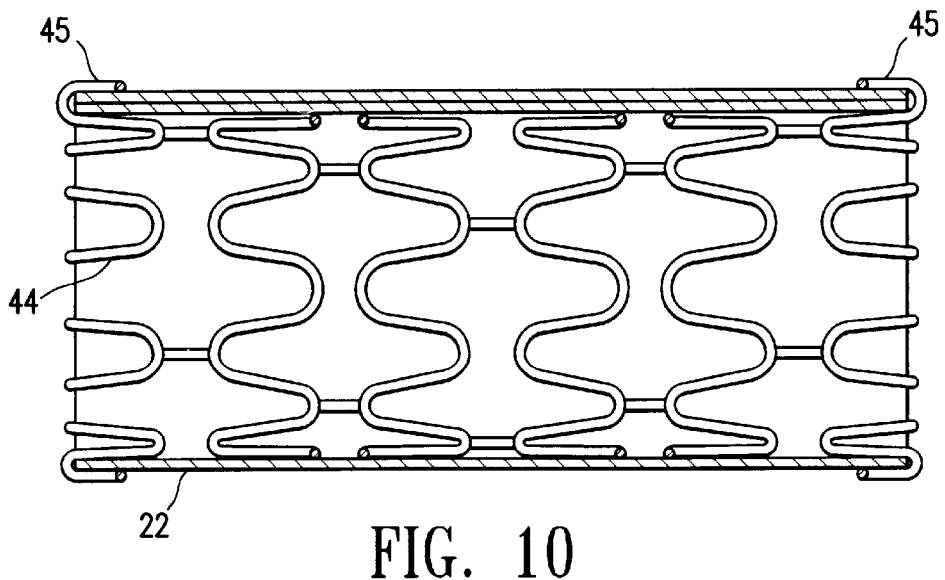
FIG. 10 is a longitudinal cross sectional view of the stent assembly shown in FIG. 9, taken along lines 10—10.

FIG. 8 illustrates an alternative embodiment of a stent 40 embodying features of the invention, comprising an expandable tubular body having a first end 41, a second end 42, and a midpoint 43 therebetween, and a framework of spaced apart wall sections 44 defining an open-walled structure. The stent 40 has at least one cover connector 45 secured to an end of the tubular body. The cover connector 45 has an open configuration, and a closed configuration in which the connector extends toward the midpoint of the tubular body, and is configured to fold from the open configuration to the closed configuration to contact a cover 22 located between the cover connector and a surface of the stent. In the embodiment illustrated in FIG. 8, the stent has a plurality of cover connectors secured about a circumference of the first end and the second end of the tubular body of the stent. FIG. 9 illustrates the cover connectors 45 in the closed configuration in which the cover connector is folded so that at least a section of the cover 22 is between the cover connector and the outer surface of the stent with an outer surface of the cover 22 in contact with the cover connector. As best illustrated in FIG. 10 showing a longitudinal cross section of the assembly shown in FIG. 9 taken along lines 10—10, the connectors 45 are folded in the closed configuration so that they have a surface which is substantially parallel to a surface of the tubular body for maximum contact with the cover. By substantially parallel, it should be understood that the surface of the cover connectors 45 adjacent to the cover is completely or nearly completely in contact with the cover. As illustrated in FIG. 10, the edges 33/34 of the cover 22 extending the length of the cover are overlapping. However, in an alternative embodiment (not shown), the edges of the cover are abutting. In this embodiment, one cover connector 45 preferably contacts both edges of the cover to hold the two edges securely together. One or more of the cover connectors 13 may be provided on stent 40, together with cover connectors 45. In one embodiment, the cover connectors 13 are provided on the ends of stent 40 together with cover connectors 45.

In the embodiment illustrated in FIG. 8, the connector 45 is a loop, and is formed by a wire or ribbon, which provides for optimal surface contact between the cover and the cover connector without forming a disadvantageous barrier between the cover and the vessel wall in which the stent assembly will be implanted. However, it would be obvious that a variety of other suitable shapes may be used including discs, fingers or projections, and the like. The cover connector 45 has a length that is typically about 0.5 mm to about 10 mm, preferably about 1 mm to about 4 mm, and a width that is about 0.07 mm to about 2 mm, preferably about 0.1 mm to about 2 mm. The width of the wire or ribbon forming the connector in FIG. 8 is about 0.1 mm to about 1 mm.

Figure 11:
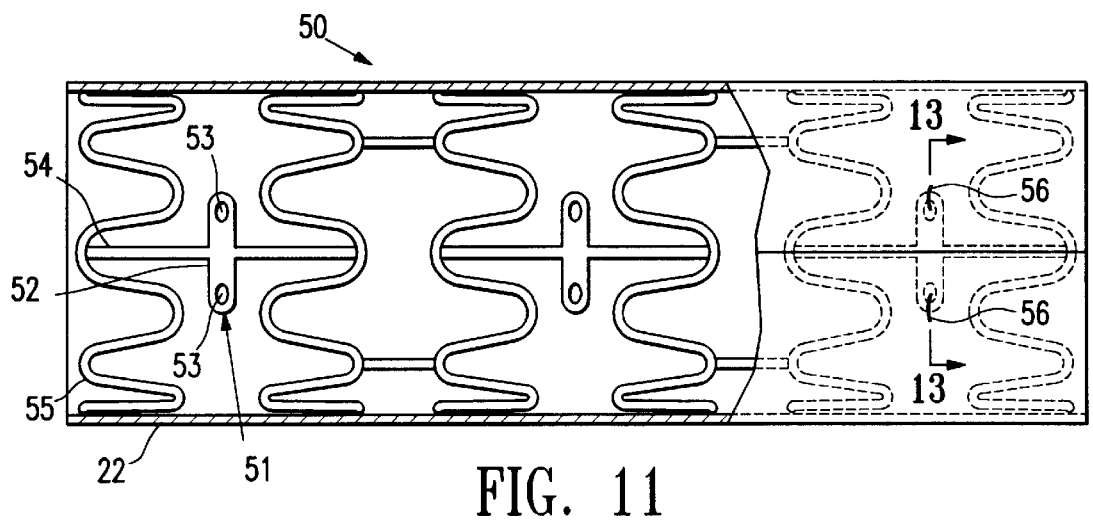
FIG. 11 is an elevational view, partially in longitudinal cross section, of a stent assembly which embodies features of the invention, having eyelet members comprising a body having eyelets in opposite ends of the body, the body being attached to a support member, and having sutures in the eyelet members connecting the cover to the stent.
Figure 13:
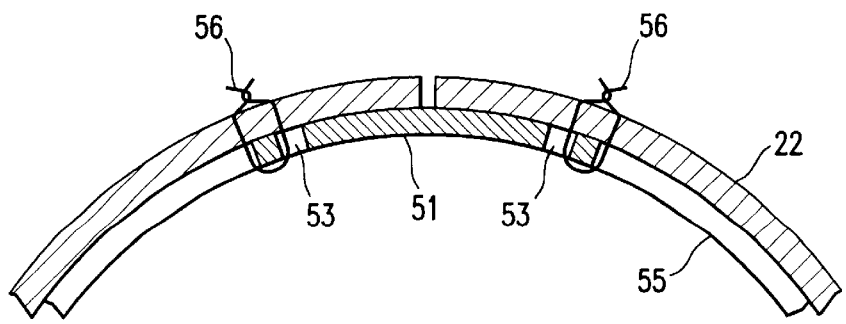
FIG. 13 is a transverse cross sectional view of the eyelet members shown in FIG. 11, taken along line 13—13.

FIG. 11 illustrates an alternative embodiment of a stent assembly 50 which embodies features of the invention, having eyelet members 51 comprising an elongated body 52 having one or more eyelets or openings 53 in opposite ends of the body 52. The body 52 is attached to a support member 54 which extends across adjacent coiled sections of stent 55. The openings 53 are configured to receive a securing member, to thereby connect cover 22 to stent 55. A variety of suitable securing members may be used including sutures, staples, hooks, and wires. In the embodiment illustrated in FIG. 11, sutures 56 are in the openings 53 to connect the cover to the stent. FIG. 13 is a transverse cross sectional view of the eyelet member 51 shown in FIG. 11, taken along line 13—13, illustrating a suture 56 in each opening 53 with knotted ends to connect cover 22 to stent 55.

Figure 12:
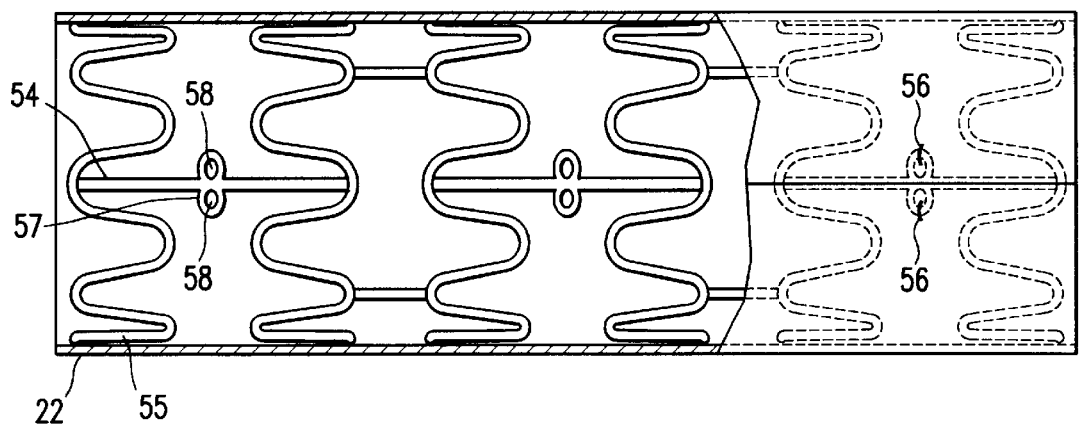
FIG. 12 is an elevational view, partially in longitudinal cross section, of an alternative embodiment of a stent assembly which embodies features of the invention having eyelet members attached to a support member, and having sutures in the eyelet members connecting the cover to the stent.

In an alternative embodiment of a stent assembly which embodies features of the invention, illustrated in FIG. 12, eyelet members 57 attached to support member 54 comprise openings 58 on either side of the support member 54, so that each opening 58 is directly adjacent to the support member 54. Sutures 56 in each opening 58 connect the cover 22 to the stent 55.

Figure 14:
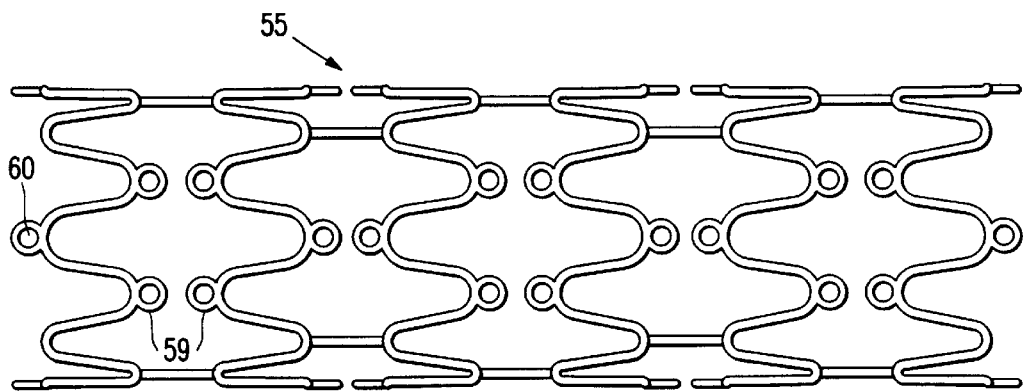
FIG. 14 is an elevational view of a stent having eyelet members comprising closed rings or loops attached to the stent, which embodies features of the invention.
Figure 15:
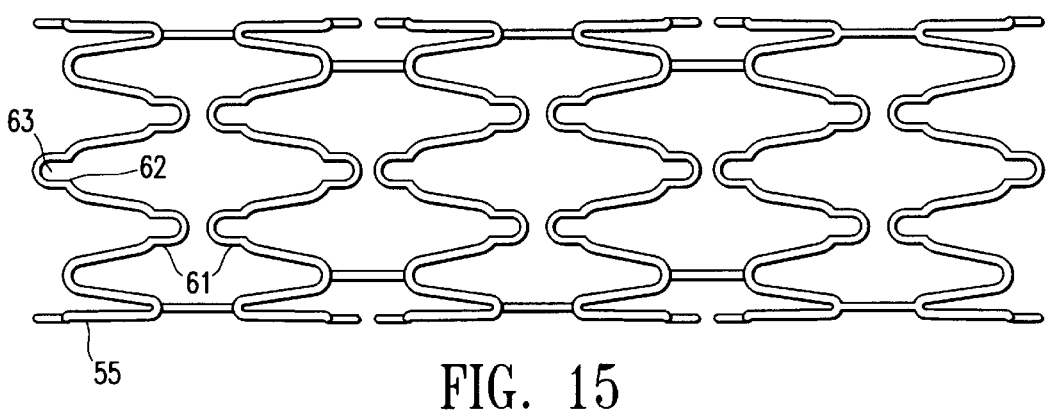
FIG. 15 is an elevational view of a stent having eyelet members comprising open rings or lopes attached to the stent, which embodies features of the invention.

FIG. 14 illustrates an alternative embodiment of a stent 55 having eyelet members 59 comprising closed rings or loops attached to the stent, which embodies features of the invention. The eyelet members 59 extend from the side of the stent 55 on the ends of the sinusoidal turns of the stent, with a central opening 60 configured to receive suture 56 or other securing member, to connect the cover 22 to the stent 55. In an alternative embodiment, eyelet members 61 are open rings or loops, as for example with an aperture 62 adjacent to the edge of the turns of the stent 55 and with an opening 63 configured to receive suture 56 or other securing member, illustrated in FIG. 15. In the embodiment of FIGS. 14 and 15, eyelet members 59 and 61 are on the top outer edge of adjacent sinusoidal turns of the stent 55. However, in alternative embodiments the eyelet members may be provided on nonadjacent turns of the stent 55 as for example on alternate turns.

Figure 16:
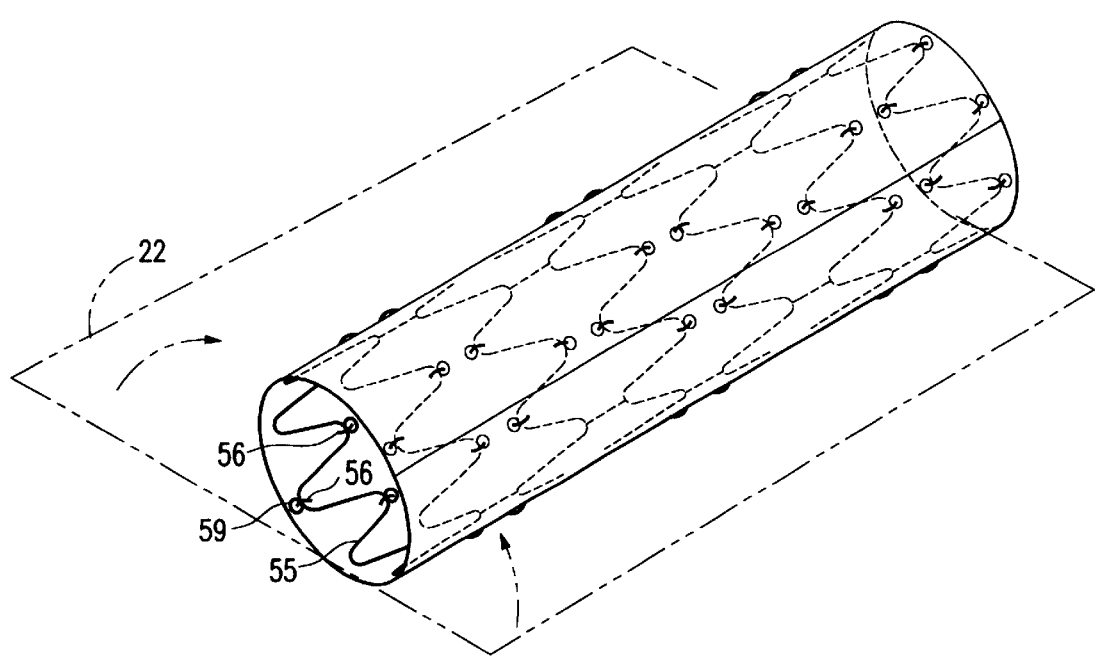
FIG. 16 is a perspective view, partially in phantom, of a stent assembly which embodies features of the invention, illustrating a cover secured to the stent by sutures in eyelet members attached to the stent.

In a presently preferred embodiment, eyelet members 51/57/59/61 are around the circumference of the stent 55. However, in alternative embodiment, eyelet members may be only along a narrow section of the stent 55 along the length of the stent 55, as illustrated in FIGS. 14 and 15, as for example, where a seam of the tubular cover 22 is located. FIG. 16 illustrates a perspective view, partially in phantom, of a stent assembly which embodies features of the invention, illustrating a cover 22 secured to the stent 55 by sutures 56 in eyelet members 59 attached to the stent 55. A variety of suitable materials may be used to form the eyelet members including stainless steel, nitinol, and tantalum. In a presently preferred embodiment, the eyelet members are formed of the same material as stent 55. The eyelet members may be formed integral with the stent, or alternatively as a separate member secured thereto, as for example by welding. Preferably, the eyelet members have the same thickness as the stent 55.

The cover 22 is preferably a biocompatible, non-thrombogenic material, such as tissue, PTFE, or DACRON. The thickness of the cover is typically from about 0.07 mm to about 1 mm, and preferably is about 0.1 mm to about 0.4 mm. The cover 22 preferably has a length configured to cover the length of the expanded stent, as illustrated in FIG. 4, showing a stent with a cover 22 extending the length of the stent, with a length equal to the stent length. However, the cover may have a length that is less than or greater than the length of the stent. The cover preferably has a circumference about equal to the circumference of the expanded stent, configured to fit on an inner or outer surface of the expanded stent. The cover preferably fits on the expanded stent so that the cover conforms to the expanded stent without flaps of excess material. The cover may be provided on the unexpanded stent in a folded or overlapping wrapped configuration which provides sufficient material which will unwrap or stretch to cover the larger circumference of the expanded stent.

The cover connectors 13/45 are preferably formed of a metallic material such as stainless steel. However, other resilient materials which are flexible enough to be bendable but stiff enough to hold the bent shape of the closed configuration can be used including platinum or nickel-titanium alloy such as nitinol. Additionally, at least a portion of first section 17 and second section 18 of cover connector 13 may be secured together, as for example by spot welding, after being bent into the closed configuration to secure the cover to the tubular body of the stent.

Stent is typically a metallic material and may comprise a variety of suitable stent designs. For example, in the embodiment where the cover connector is a separate part joined to a stent, a variety of commercially available stents may be used such as Micro Stent II and GFX stents available from Arterial Vascular Engineering, and Multi-Link, available from Guidant. Other stents that may be used in the practice of this invention include the Palmaz-Shatz stent from Johnson and Johnson, the Gianturco stent from Cook Incorporated and other commercially available stents. Conventional balloon expandable stents are preferred, but self-expanding stents, such as those formed from shape memory materials, are also suitable. The length of the stent, for coronary applications, is generally about 4 to greater than about 80 mm, typically about 5 to about 80 mm, preferably about 10 to about 50 mm. The stent generally has a diameter of about 1.5 to about 35 mm, typically about 2 to about 6 mm, preferably about 2.5 to about 5 mm. The actual length and diameter of the stent and cover may vary, and will depend on the nature of the vessel in which the stent assembly is implanted. For example, for peripheral vessel applications, such as an aortic abdominal aneurysm, a larger stent having a length of about 5 mm to about 200 mm and a diameter of about 2 mm to about 60 mm would be used.

Figure 17:
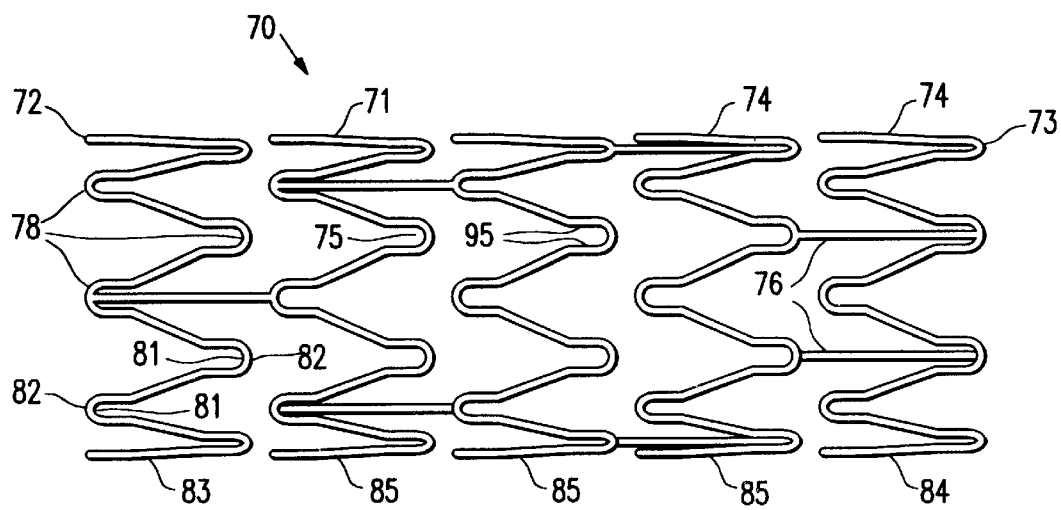
FIG. 17 is an elevational view of an alternative embodiment of a stent which embodies features of the invention.

An alternative embodiment of the invention is illustrated in FIG. 17. FIG. 17 illustrates a stent 70 generally comprising an expandable tubular body 71 having a first end 72, a second end 73, a plurality of cylindrical wall sections 74 defining an open-walled structure. The wall sections 74 are longitudinally spaced apart from one another so that each individual wall section 74 is longitudinally adjacent to at least one other wall section 74. The tubular body 71 has eyelet members 75 formed by the turns of the wall section 74. A plurality of bar members 76 are connected to the tubular body 71. As illustrated in FIG. 17, longitudinally adjacent wall sections 74 have at least one bar member 76 connected to and extending therebetween. In a presently preferred embodiment, at least two bar members 76 are connected to and extend between longitudinally adjacent wall sections 74. The bar member 76 provides support to and connects the wall sections 74, and in the illustrated embodiment comprises a solid member having a circular cross section. However, the bar member can have a variety of suitable configurations including hollow or tubular, and with circular, oblong, square, or rectangular cross sections.

In the embodiment illustrated in FIG. 17, each wall section 74 comprises a curvilinear member which extends around a circumference of the tubular body 71 and which has a plurality of turns 78, each turn having a concave surface 81 facing in a direction opposite to the concave surface 81 of a radially adjacent turn 78 on the same wall section as the turn, and a convex surface 82 facing in a direction opposite to the convex surface 82 of a radially adjacent turn 78 on the same wall section as the turn. The juncture between radially adjacent turns on a wall section 74 is at the longitudinal midpoint along the length of the wall section 74. Each bar member 76 is connected to and extends between the concave surface 81 of a turn 78 and the convex surface 82 of a turn 78 on a longitudinally adjacent wall section. In the embodiment of FIG. 17, the turns 78 of an individual wall section 74 are in phase with the turns of a longitudinally adjacent wall section 74. The terminology "in phase" should be understood to mean that the turns 78 are lined up along the length of the stent, with turns 78 on a wall section 74 facing in the same direction as the turns in line therewith on the longitudinally adjacent wall section 74. In contrast, in the embodiment illustrated in FIG. 1, the turns of a wall section 12 are out of phase with the turns on the adjacent wall section 12. In a presently preferred embodiment of the stent illustrated in FIG. 17, the turns 78 are in phase with the turns 78 of the adjacent wall section 74. As a result, the manufacture of the stent 70 is facilitated, and the length of the bar member 76 is relatively short and provides a relatively strong connection between adjacent wall sections 74 as compared to a bar member connecting turns 78 which are out of phase. However, in an alternative embodiment of stent 70, the turns 78 of longitudinally adjacent wall sections 74 are out of phase with one another (not shown), wherein each bar member 76 is connected to and extends between the concave surface 81 of a turn 78 and the concave surface 81 of a turn 78 on a longitudinally adjacent wall section 74.

The stent 70 has a first wall section 83 at the first end of the tubular body, a second wall section 84 at the second end of the tubular body, and intermediate wall sections 85 located between the first and second wall sections 83/84. The turns 78 of the first wall section 83 which have convex surfaces 82 which face toward the intermediate wall sections 85 are not connected to a bar member 76, i.e., the convex surfaces of the turns closest to the adjacent intermediate wall section 85 are not directly connected by a bar member or other member to the adjacent intermediate wall section 85. Consequently, a first section of a cover can be disposed on a surface of the intermediate wall sections 85 with a second section of the cover disposed on an opposite surface of the first and/or second wall section 83/84. More specifically, the ends of a cover can be placed under the first and second wall sections 83/84 while the intermediate section of the cover is over the intermediate section of the stent.

Figure 18:
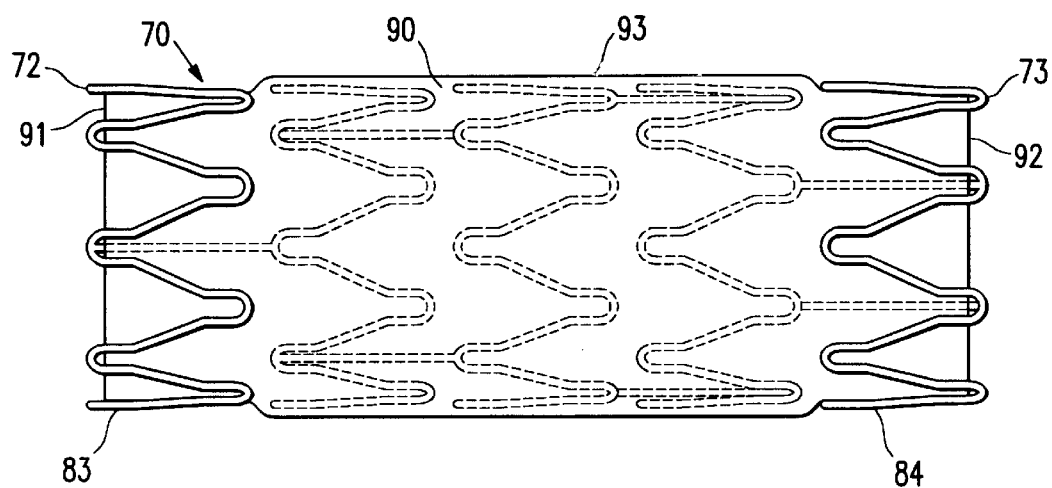
FIG. 18 is an elevational view of the stent shown in FIG. 17 having a cover on the stent.
Figure 19:
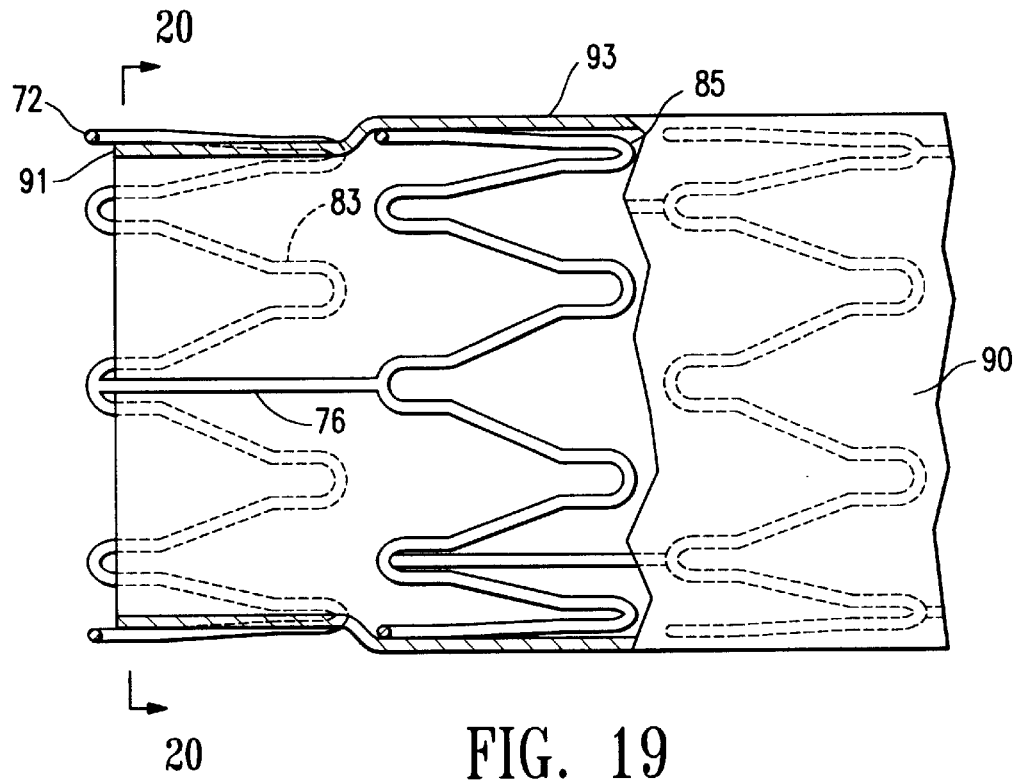
FIG. 19 is fragmentary sectional view of the stent and cover assembly shown in FIG. 18.
Figure 20:
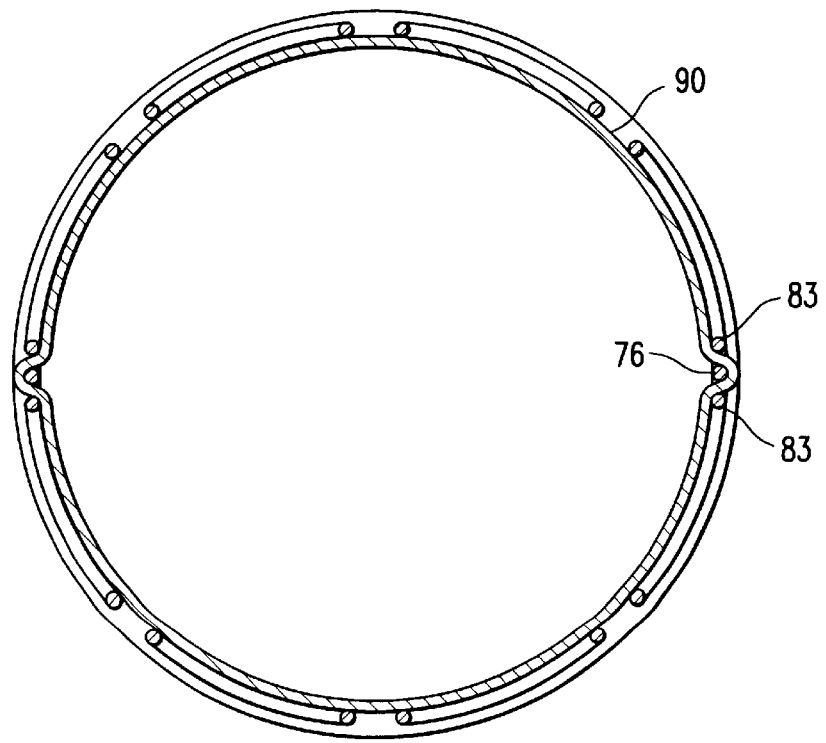
FIG. 20 is a transverse cross sectional view of the stent and cover assembly shown in FIG. 18, taken along line 20—20.

FIG. 18 illustrates the stent 70 shown in FIG. 17 with a cover 90 on the stent 70. The cover has a first end 91, a second end 92 and an intermediate section 93 between the first and second ends 91/92. As best illustrated in FIG. 19, showing a fragmentary sectional view of covered stent at the first end 72 of the stent, with the cover 90 partially broken away, the first end 91 of the cover is adjacent to an inner surface of the first wall section 83. Similarly the second end 92 of the cover is adjacent to an inner surface of the second wall section 84. Conversely, the intermediate section 93 of the cover is adjacent to an outer surface of the intermediate sections 85. In an alternative embodiment, the intermediate section 93 is adjacent an inner surface of the intermediate sections 85, and the first and second ends 91/92 of the cover are adjacent an outer surface of the first and second wall sections 83/84 (not shown). While discussed primarily in terms of having both the first and the second end 91/92 of the cover 90 on an opposite surface from the cover intermediate section 93, it should be understood that only one end of the cover may be so disposed with the opposite end on the same surface of the stent 70 as the intermediate section 93 of the cover 90.

The inner surface of the first end 91 of the cover is adjacent to an outer surface of the bar members 76 which extend between the first wall section 83 and the intermediate wall section 85 longitudinally adjacent thereto. Similarly, the inner surface of the second end 92 of the cover is adjacent to an outer surface of the bar members 76 which extend between the second wall section 84 and the intermediate wall section 85 longitudinally adjacent thereto. Consequently, the first end 91 of the cover 90 is disposed between the first wall section 83 and the bar members 76 secured thereto, and the second end 92 of the cover 90 is disposed between the second wall section 84 and the bar members 76 secured thereto. In a presently preferred embodiment, at least one bar member 76, and most preferably two bar members 76, are connected to and extend between the first wall section 83 and the intermediate wall section 85 longitudinally adjacent thereto, and at least one bar member 76, and most preferably two bar members 76, are connected to and extend between the second wall section 84 and the intermediate wall section 85 longitudinally adjacent thereto. However, any number of bar members 76 can be provided as are desired for providing sufficient stability to the tubular body of the stent. The ends of the cover 90 disposed on an opposite surface of the stent 70 to the intermediate section of the cover 90, and between the bar member 76 and the turns 78 of the first and second wall sections 83/84, is thus attached to the stent without folding the ends of the cover around the ends of the stent from one surface of the stent to the opposite surface of the stent. Consequently, the covered stent of the invention has a low profile, and improved trackability by reducing the tendency of the cover to get caught or engaged in tight spaces within the arterial lumen during advancement of the covered stent.

The first and second wall sections 83/84 are sufficiently flexible to allow for bending up above the outer surface of the intermediate wall sections 85, or down below the inner surface of the intermediate wall sections 85, to facilitate placing the ends 91/92 of the cover 90 between the first and second wall sections 83/84 and the bar members 76 connected thereto. The wall sections 74 are preferably formed of metal such as stainless steel.

In one embodiment, the cover 90 has a length substantially equal to the length of the stent 70. Substantially equal to should be understood to include a cover 90 with a length equal to, or not more than about 5% less than, or not more than about 5% greater than the length of the stent. In alternative embodiments, the cover has a length less than the length of the stent so that the stent is partially covered (not shown). In one embodiment having a partially covered stent, the cover is on the intermediate wall sections 85, and the ends of the stent are not covered. Thus, the cover is disposed over at least one intermediate wall section 76 and under at least a second intermediate wall section 85, so that the cover is disposed between an intermediate wall section 85 and the bar member(s) 76 which connect the intermediate wall section 85 to an adjacent intermediate wall section 85. The partially covered stent having the cover on a middle section of the stent is particularly preferred for use applications such as Trans Jugular Intra-hepatic Portal Shunts (TIPS). In another embodiment having a partially covered stent, the cover comprises two separate members on either end of the stent with one or more intermediate sections of the stent not covered, or a single cover on one end of the stent with the remaining sections of the stent uncovered, the cover having an end disposed between the first and/or the second wall section 83/84 and the bar member(s) 76 connected thereto, in accordance with the invention as discussed above. The partially covered stent having the cover on an end section of the stent is particularly preferred for use at the site of a branch lumen, so that an uncovered middle section of the stent is provided which does not occlude the branch lumen.

In the embodiment illustrated in FIG. 18, the ends 91/92 of the cover 90 do not extend beyond the ends 72/73 of the stent 70. In the embodiment illustrated in FIGS. 18 and 19, the first and second ends 91/92 of the cover 90 are in contact with the concave surfaces 81 which face toward the intermediate wall sections 85. Alternatively, the cover 90 may have a shorter length with the first and second ends 91/92 of the cover in contact with sections of the turns 78 of the first and second wall sections 83/84, respectively, which are closer to the intermediate wall sections 85. In a presently preferred embodiment, the cover 90 is first formed into a cylinder, as by sewing the edges of the sheet of material used to form the cover together, and then placed around the stent with the ends of the cover under the first and second wall sections 83/84. The edges of the cover are preferably facing and abutting one another to provide a low profile configuration, however, in alternative embodiments they may be in an overlapping relationship to one another.

Figure 21:
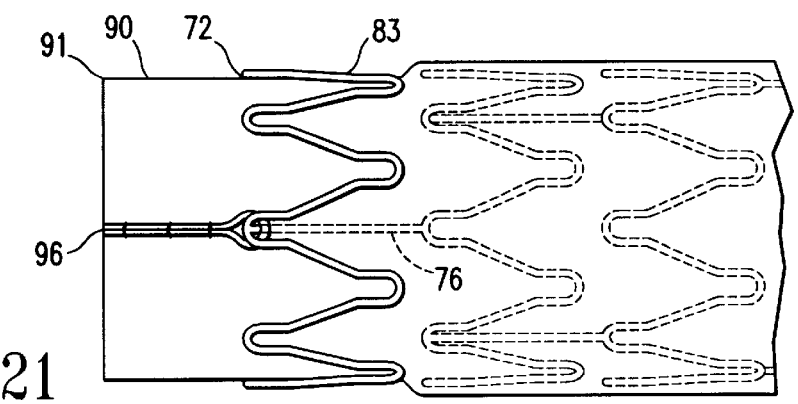
FIG. 21 is an elevational partial view, partially in phantom, of an alternative embodiment which embodies features of the invention, having a cover extending beyond a first end of the stent.
Figure 22:
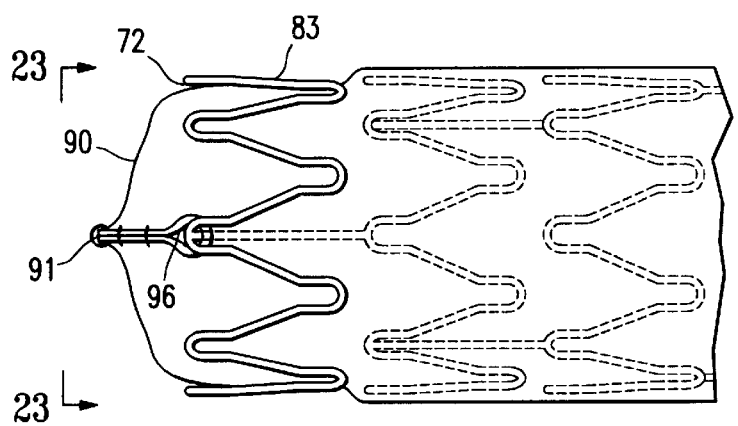
FIG. 22 is an elevational partial view, partially in phantom, of the covered stent shown in FIG. 21, having the edges of the extended end of the cover joined together.
Figure 23:
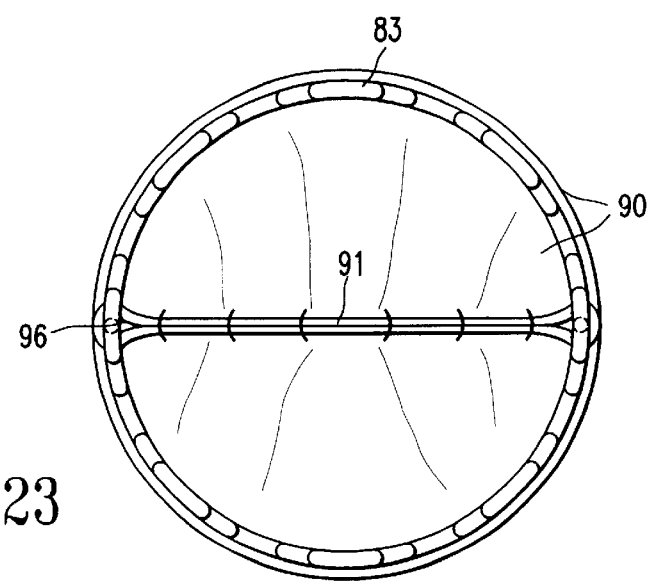
FIG. 23 is a transverse view of the covered stent shown in FIG. 22 taken along line 23—23.

In an alternative embodiment, one or both ends 91/92 of the cover may extend beyond the ends 72/73 of the stent. In the embodiment illustrated in FIG. 21, the cover has a slit 96 in the first end 91 of the cover 90, which allows the first end 91 of the cover 90 to extend beyond the first end 72 of the stent. The end of the first wall section 83 of the stent, at the location at which the bar member 76 is attached thereto, is within the slit so that the connection between the first wall section 83 and the bar member 76 does not block the end of the cover from extending beyond the end of the stent. After the cover 90 is in place on the stent with the end of the cover extending beyond the stent end, the cut edges of the cover defining the slit 96 are reconnected together, as for example by suturing as illustrated in FIG. 21, or with other connecting methods such as staples or bonding with adhesive or fusing. In the embodiment having the end of the cover extending beyond the end of the stent, the end of the cover can be closed off before the covered stent assembly is introduced into the patient's body lumen. After the covered stent is implanted in the body lumen, the closed end of the cover thus closes or occludes the body lumen to prevent or inhibit fluid flow therein. FIG. 22 illustrates the covered stent assembly of FIG. 21, after the edges of the open end 91 of the cover 90 have been brought together and secured to close off the end of the cover. The end of the cover is closed off using sutures, as best illustrated in FIG. 23 which illustrates a transverse view of the end of the covered stent shown in FIG. 22, taken along line 23—23. However, the end of the cover can be closed off using a variety of suitable methods including stapling, and bonding with adhesives or fusing.

In the embodiment illustrated in FIG. 17, stent 70 has eyelet members 75 at either end of the wall sections 74. The eyelet members 75 are open loops defined at least in part by the concave surface 81 of the turn 78 of the wall section 74. However, a variety of suitable eyelet members may be provided including the closed loop eyelet members which are on the tubular body or on support members or bar members extending between longitudinally adjacent wall sections 74 as discussed above in relation to the embodiments of FIGS. 11, 12 and 14. The eyelet members 75 at the center of a turn 78 have parallel sides 95 and a smaller inner diameter than sections of the turn adjacent to the eyelet member 75. The turns 78 have sections which taper to the smaller diameter eyelet members 75. In a presently preferred embodiment, sutures (not shown) are provided along the length and around the circumference of the stent 70 through eyelet members 75, connecting the cover 90 thereto. However, in alternative embodiments, sutures are provided intermittently or at selected locations on the stent 70.

In a presently preferred embodiment of the stent assembly of FIG. 18, the cover 90 is heterologous tissue such as pericardium, leaflet, veins, arteries, and the like. However, synthetic materials including fluoropolymers such as PTFE and polyesters such as Dacron can also be used. Preferably the cover 90 is sufficiently compressible to allow the cover 90 to be compressed between the first and second wall sections 83/84 and the bar members 76 connected thereto. The cover preferably has a thickness of about 0.001 mm to about 2 mm, and most preferably about 0.10 mm to about 0.15 mm. The tissue may be thinned by cutting layers of tissue away, to provide a sufficiently thin cover 90.

FIGS. 17–23 illustrate all the wall sections 74 of the stent having a configuration with turns 78 connected by bar members 76 to longitudinally adjacent wall sections 74. However, it should be understood that the intermediate wall section(s) 85 may have a variety of configurations including comprising one continuous member extending around the stent circumference. Thus, in one embodiment only the first and second wall sections 83/84 at the ends of the stent 70 comprises the turns 78 connected by bar members 76 to the adjacent wall section as illustrated, so that the stent is configured to allow the cover to be disposed under the first and second wall sections 83/84 at the ends of the stent 70, and over the intermediate wall section(s) 85. Additionally, while discussed and shown in terms of rounded wall section turns 78 having concave and convex surfaces 81/82, it should be understood that the turns 78 of the wall section 74 may comprises angled surfaces having a V-shaped configuration, with internal and external surfaces at a central section of the turn which are more sharply angled than the more gradually curved surfaces 81/82 illustrated in FIG. 17.

Although primarily described with respect to preventing restenosis in angioplasty patients, the covered stents of this invention may be used in a number of coronary artery, peripheral artery and non-vascular applications. For example, coronary artery applications include use in ectatic arteries and ectatic arteries containing an obstructive lesion, aneurismatic arteries, saphenous vein grafts and native arteries, coronary perforation, coronary fistula, and ostial coronary lesions. Peripheral artery applications include aortic abdominal aneurysm and other aneurismatic peripheral arteries, transjugular intrahepatic portal shunt, percutaneous transluminal angioplasty, fistula closing and neuro interventions (such as aneurysms and arterial-venous malformations), small vessel intraluminal grafting, and ostial renal artery lesions. Finally, the covered stents of this invention may be used in urological, gastroenterological, respiratory, neurological, and other non-vascular applications. For example, urological field applications include urethral stenting for stenosis due to tumors, fibrous tissue and perforation. Gastroenterological field applications include fistula closing, reconstruction such as esophagus reconstruction, and esophageal bleeding. Respiratory field applications include tracheal and bronchial obstructions, and neurological field applications include carotid angioplasty.

A general description of the device of the present invention as well as a preferred embodiment of the present invention has been set forth above. One skilled in the art will recognize and be able to practice many changes in many aspects of the device described above, including variations that fall within the teachings of this invention. For example, although the cover is illustrated on the outer surface of the stent, a cover may be secured to an inner surface of the stent using the cover connectors of the invention. Additionally, although the cover is illustrated primarily in terms of a sheet of material forming a cylinder about the stent, the cover connectors may be used to attach a variety of covers. to the stent such as ribbons of material wrapped in whole or in part about the stent. The stent assembly may be used in branched body lumens, and positioned to block one or more of the branch lumens or reconstruction of bifurcations by a specially tailored bifurcated cover stent.

What is claimed is:

1. A stent assembly, comprising:

a) a stent comprising i) an expandable tubular body having a first end, a second end, a plurality of interconnected cylindrical wall sections including a first cylindrical wall section at the first end of the tubular body, a second cylindrical wall section at the second end of tubular body, and at least one intermediate cylindrical wall section between the first and second cylindrical wall sections, and ii) each of the interconnected cylindrical wall sections are secured to at least one longitudinally adjacent cylindrical wall section by one or more connecting bar members connected to the tubular body, so that at least one bar member is connected to and extends between two longitudinally adjacent wall sections; and b) a cover having a first end, a second end, and an intermediate section between the first and second ends, wherein the first end of the cover is disposed under a portion of the first cylindrical wall section and on top of at least one connecting bar member connected thereto and a longitudinally adjacent cylindrical wall section.

2. The stent assembly of claim 1 wherein at least one connecting bar member is connected to and extends between the second cylindrical wall section and an intermediate cylindrical wall section longitudinally adjacent to the second cylindrical wall section.

3. A stent assembly, comprising:
   a) a stent comprising
      i) an expandable tubular body having a first end, a second end, a plurality of interconnected cylindrical wall sections including a first cylindrical wall section at the first end of the tubular body, a second cylindrical wall section at the second end of tubular body, and at least one intermediate cylindrical wall section between the first and second cylindrical wall sections; and
      ii) each of the cylindrical wall sections of the tubular body having at least one connecting bar member is connected to and extending between a longitudinally adjacent cylindrical wall section; and
   b) a cover having a first end cover section, a second end cover section, and at least one intermediate cover section between the first and second ends cover sections, wherein the first end cover section is secured under a portion of the first cylindrical wall section of the tubular body, the second end cover section under a portion of the second cylindrical wall section of the tubular body, and the intermediate cover section is on an outer surface of at least one intermediate cylindrical wall section.

4. The stent assembly of claim 3 having a first connecting bar member extending between the first wall section and a longitudinally adjacent wall section and a second connecting bar member extending between the second wall section and a longitudinally adjacent wall section, and wherein the inner surface of the first end of the cover is adjacent an outer surface of the first connecting bar member, and the inner surface of the second cover end is adjacent an outer surface of the second connecting bar member.

5. The stent assembly of claim 3 wherein the first cylindrical wall section is provided with a plurality of undulations and the cover first end is in under at least one undulation of the first cylindrical wall section.

6. A stent assembly comprising:
   a. an expandable tubular stent body which has first and second ends, a plurality of interconnected ring sections including a first ring section at the first end, a second ring section at the second end and at least one intermediate ring section disposed between the first and the second ring sections with each of the interconnected ring sections being secured to at least one longitudinally connected ring sections by at least one connector extending between and secured to at least one adjacent ring section; and
   b. a stent cover which is formed of bio-compatible material, which has a first cover section, a second cover section and an intermediate cover section between the first and second cover sections, which has at least part of a first cover section disposed under a portion of the first ring section and on a connector extending between the first ring section and an adjacent ring section.

7. The stent assembly of claim 6 wherein the second cover section is disposed under a portion of the second ring section and on a plurality of connectors extending between the second ring section and an adjacent ring section.

8. The stent assembly of claim 6 wherein a plurality of connectors extend between the first ring section to an adjacent intermediate ring section.

9. The stent assembly of claim 6 wherein the first and second ring sections have a plurality of undulations.

10. The stent assembly of claim 9 wherein undulations are the portions of the ring sections under which the end cover sections are disposed.

* * * * *